United States Patent
Ross

(10) Patent No.: US 7,476,231 B2
(45) Date of Patent: Jan. 13, 2009

(54) OBSTETRICAL VACUUM EXTRACTOR

(76) Inventor: Michael G. Ross, 1142 Somera Rd., Los Angeles, CA (US) 90077

(*) Notice: Subject to any disclaimer, the term of this patent is extended or adjusted under 35 U.S.C. 154(b) by 577 days.

(21) Appl. No.: 11/301,593

(22) Filed: Dec. 13, 2005

(65) Prior Publication Data

US 2006/0161175 A1    Jul. 20, 2006

Related U.S. Application Data

(60) Provisional application No. 60/635,209, filed on Dec. 13, 2004.

(51) Int. Cl.
*A61B 17/42* (2006.01)
(52) U.S. Cl. ...................................................... 606/123
(58) Field of Classification Search .............. 606/123, 606/119, 122, 124; 604/540, 74, 268, 264, 604/275, 278, 279, 541, 542, 73, 75, 76, 604/77
See application file for complete search history.

(56) References Cited

U.S. PATENT DOCUMENTS

| | | | |
|---|---|---|---|
| 3,202,152 A | 8/1965 | Wood | |
| 3,765,408 A * | 10/1973 | Kawai | 606/213 |
| 3,860,001 A * | 1/1975 | Levin | 604/279 |
| 5,019,086 A | 5/1991 | Neward | |
| 5,281,229 A | 1/1994 | Neward | |
| 5,569,265 A * | 10/1996 | Elliott | 606/123 |
| 5,935,136 A * | 8/1999 | Hulse et al. | 606/123 |
| 5,957,931 A * | 9/1999 | Dimitriu | 606/123 |
| 6,179,845 B1 * | 1/2001 | Peters et al. | 606/123 |
| 6,361,542 B1 | 3/2002 | Dimitriu et al. | |
| 6,506,166 B1 * | 1/2003 | Hendler et al. | 600/562 |
| 6,723,105 B1 * | 4/2004 | Hulse et al. | 606/123 |

* cited by examiner

*Primary Examiner*—Todd E Manahan
*Assistant Examiner*—Sarah A Simpson
(74) *Attorney, Agent, or Firm*—Gifford, Krass, Sprinkle, Anderson & Citkowski, P.C.

(57) ABSTRACT

An obstetrical vacuum extractor has a bell-shaped cup with an open edge in communication with a hollow stem. A plurality of apertures in the cup prevent a vacuum from being drawn within the cup when the open end is brought into contact with a fetal scalp, in the absence of a sheet liner adapted to fit within the interior of the cup, engage its open edge, and having a central hole adapted to communicate with the hollow stem so that a vacuum may be drawn within the liner. The liner surface preferably includes a foil layer and covers the apertures so that the vacuum may be drawn.

4 Claims, 1 Drawing Sheet

OBSTETRICAL VACUUM EXTRACTOR

REFERENCE TO RELATED APPLICATION

This application claims priority to U.S. provisional patent application Ser. No. 60/635,209, filed Dec. 13, 2004, the contents of which are incorporated herein in its entirety.

FIELD OF THE INVENTION

This invention relates to an obstetrical vacuum extractor and, more particularly, to such extractors incorporating a resilient vacuum cup adapted to be placed onto the scalp of a fetus and provided with ventilation holes which prevent a vacuum from being drawn within the cup unless a disposable sheet liner is disposed within the cup to block the holes.

BACKGROUND OF THE INVENTION

Vacuum extractors for use in childbirth may employ a bell-shaped vacuum cup with a resilient edge adapted to be placed on the scalp of a fetus in the birth canal. A vacuum passage in an elongated hollow stem connects to the interior of the cup through a central hole in the cup and the other end of the stem is connected to a vacuum pump. The vacuum pressure within the cup results in a suction force being applied between the cup and the head which adheres the cup to the fetal scalp. Once the cup is positioned on the head of the fetus, the vacuum extractor can then be used to extract the fetus from the birth canal by manipulating the stem through a handle, or the like.

Devices of this general type are disclosed in U.S. Pat. Nos. 5,019,086, 5,281,229, and 6,361,542. In the United States, vacuum cups typically formed of synthetic plastic and adapted to be disposed after a single use, are generally employed. However, the disposable cups are cost prohibitive in much of the developing world. Sale of disposable cups which are intended for a one-time use, often results in the cup being used multiple times, with issues of sterility, damage to the cup apparatus from multiple use, and tearing of the cup surface which is applied to the fetal scalp.

It would be highly desirable to provide a vacuum cup which is capable of multiple uses, but is designed so as to provide a new, sterile surface for each use. U.S. Pat. No. 5,281,229 discloses an obstetrical vacuum extractor having a liner 30 permanently secured to the interior of the vacuum cup so as to present a soft, flexible surface adapted to contact and line the interior of the vacuum cup. This liner has a central hole 48 which communicates the vacuum provided through the stem to the interior of the cup. The liner is not removable, but is rather welded or otherwise secured to the cup.

SUMMARY OF THE INVENTION

The present invention is accordingly directed toward an obstetrical vacuum extractor having ventilation holes in the vacuum cup, which prevents the vacuum from being drawn with the cup, unless it is used with a single-use, sterile liner for the cup which includes a soft cup edges adapted to be attached to the scalp. The liner seals the ventilation holes in the cup and allows a vacuum to be drawn within the cup so that it may be used for extractions. The liner is removed with each use and must be replaced with another sterile liner before the next use of the extractor. This invention thus provides a low-cost, highly sterile, reusable vacuum extractor.

DETAILED DESCRIPTION OF THE DRAWINGS

Other objects, advantages and applications of the present invention will be made apparent by the following detailed description of the preferred embodiments of the invention. The description makes reference to the accompanying drawings in which.

DETAILED DESCRIPTION OF THE INVENTION

Figure 1:
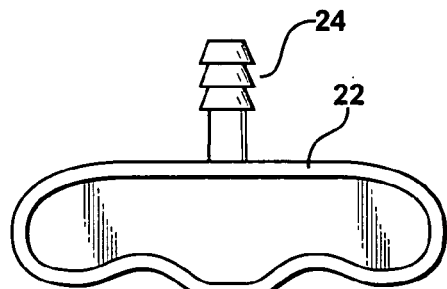
FIG. 1 is a side view of a preferred embodiment of my obstetrical vacuum extractor.
Figure 2:
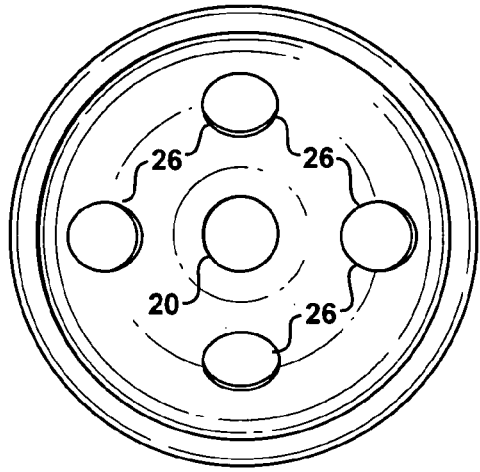
FIG. 2 is a bottom view of the extractor of FIG. 1, taken along lines 2-2 of FIG. 1.

Referring to the drawings, the obstetrical vacuum extractor, generally indicated at 10 in FIG. 1, is of the type that has been used for many years and is generally disclosed in U.S. Pat. Nos. 3,202,152 and 5,019,086, as well as others. It generally consists of a vacuum cup 12 which is generally bell-shaped in configuration and has an open end 14 with a lip 16. A hollow stem 18 connects to the interior of the vacuum cup 12 through a central hole 20, visible in FIG. 2. The stem has a handle 22 used to manipulate the extractor and the upper end of the stem has a ribbed configuration 24, adapted to receive a resilient hose connecting to a vacuum source (not shown).

Figure 5:
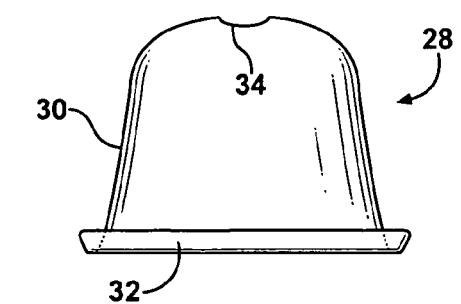
FIG. 5 is a side view of a sanitary, disposable liner for the extractors of either FIG. 1 or FIG. 3.

The vacuum extractor of the present invention differs from prior art extractors of this general type by virtue of its incorporation of a series of holes or perforations 26, formed through the cup 12. The purpose of the perforations 26 is to prevent use of the extractor in the absence of a cup liner of the type generally indicated at 28 in FIG. 5. If the extractor 10 were to be used without a liner, when the resilient edge 16 of the cup 12 is brought in contact with the head of a fetus, a vacuum could not be drawn because the vacuum source supplied to the stem 18 would simply draw ambient air through the openings 26 and prevent creation of a seal between the resilient edge 16 and the fetal head.

In order to draw a seal, it is necessary to place a liner over the interior of the cup 12. Liner 28 preferably has a foil exterior 30 and a resilient edge 32 which is pressed against the fetal scalp. The edge 32 is upturned to form a cuff which extends over the outer edge 16 of the cup 12. A central hole 34 at the top of the liner mates with the hole 20 on the top of the cup 12 so that the vacuum communicated through the hollow stem 18 draws the air from the interior of the liner 28. The liner 28 is placed over the cup and the extractor is then ready for obstetrical use. The lip 32 of the liner is brought into contact with the fetal scalp and the vacuum is applied through the stem 18 to seal the scalp to the liner and the extractor. This vacuum retains the seal 28 snugly within the interior of the cup 12. The liner provides sterile contact with the fetal scalp.

After the extraction and the removal of the vacuum source, the liner 28 can no longer be retained to the interior of the cup and will fall off and be discarded. This makes reuse of the liner totally impractical and a clean, sterile liner is used for the next extraction.

Figure 3:
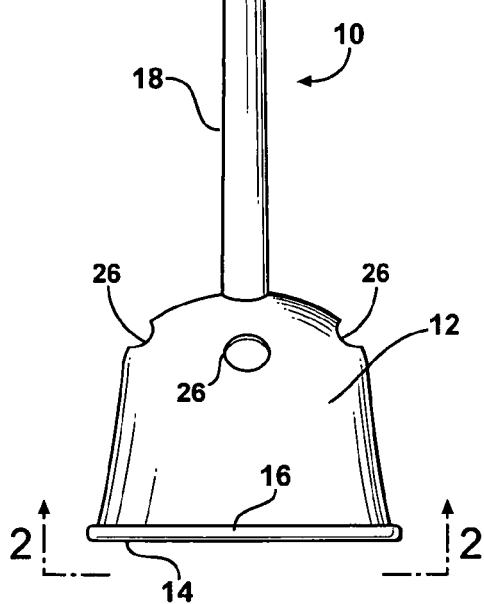
FIG. 3 is a partial view of an alternative embodiment of my extractor, having a scalloped edge to the suction cup rather than the holes in the embodiment of FIG. 1.
Figure 3:
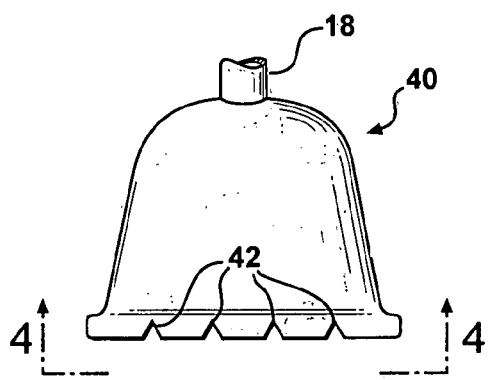
Figure 4:
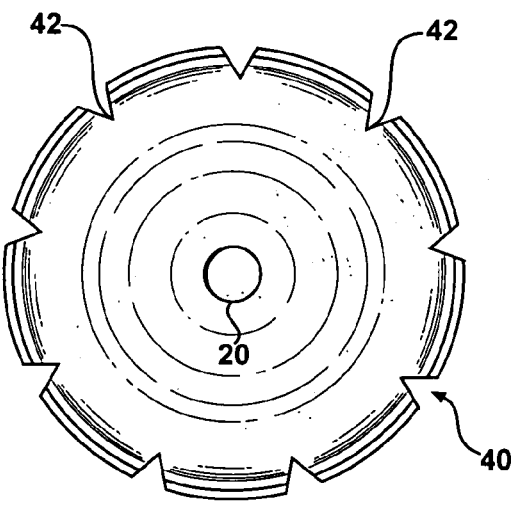
FIG. 4 is a bottom view of the embodiment of FIG. 3, taken along lines 4-4 of FIG. 3.

FIGS. 3 and 4 illustrate an alternative form of cup 12 for the extractor. Rather than having holes 26 formed near its top, the extractor cup generally indicated at 40 in FIGS. 4 and 5, has a scallop 42 formed about its edge. The scallop prevents a vacuum from being drawn within the cup 40 in the same way that the perforations 26 prevent a vacuum, in the absence of a liner of the same general type indicated at 28. The cuff 32 of the liner 28 covers the scallops 42, allowing a seal to be drawn between the edge of the liner and fetal scalp by virtue of the vacuum drawn through the hole 20 in the center of the cup 40.

By allowing reuse of the main structural parts of the vacuum extractor and providing a low-cost, inherently disposable sheet liner for the interior of the cup, the present invention solves the problem of providing a cost-effective vacuum extraction solution for low-cost reuse.

I claim:

1. A vacuum extractor adapted to be applied to a fetal scalp, comprising:
   a bell-shaped cup having an open edge;
   an elongated, hollow stem communicating at one end with the cup and at the opposite end with a vacuum source;
   a plurality of relief areas formed in the cup which prevent a vacuum from being drawn within the cup when a vacuum supplied from the source and the open edge of the cup is brought into contact with a fetal scalp; and
   a sheet liner adapted to be inserted into the interior of the cup and having a central hole adapted to communicate with the interior of the hollow stem and a surface adapted to close off the relief areas so as to allow a vacuum to be drawn when the extractor cup, with the liner, is inserted into contact with a fetal scalp.

2. The extractor of claim 1, in which the relief areas comprise holes formed in the surface of the cup.

3. The extractor of claim 1, in which the relief areas comprise scallops formed along the edge of the cup.

4. The extractor of claim 1, wherein the liner is formed of sheet material having a foil layer.

* * * * *